United States Patent [19]

Drutz et al.

[11] Patent Number: 4,722,891
[45] Date of Patent: Feb. 2, 1988

[54] METHODS AND COMPOSITIONS FOR DETECTION OF LEGIONNAIRES' DISEASE

[75] Inventors: David J. Drutz; Barry I. Eisenstein; N. Cary Engleberg, all of San Antonio, Tex.

[73] Assignee: Board of Regents, The University of Texas System, Austin, Tex.

[21] Appl. No.: 622,567

[22] Filed: Jun. 20, 1984

[51] Int. Cl.[4] .................. C12N 15/00; G01N 33/531; G01N 33/554
[52] U.S. Cl. .......................................... 435/7; 435/68; 435/172.3; 436/519; 436/543; 530/806; 530/808; 530/810; 530/825; 935/73
[58] Field of Search .................. 935/73; 435/172.3, 7, 435/68; 436/543; 530/806, 808, 825, 810

[56] References Cited

U.S. PATENT DOCUMENTS

| | | | |
|---|---|---|---|
| 4,336,336 | 6/1982 | Silhavy et al. | 435/172 |
| 4,358,535 | 11/1982 | Falkow et al. | 435/5 |
| 4,394,443 | 7/1983 | Weissman et al. | 435/6 |
| 4,431,739 | 2/1984 | Riggs | 435/253 |
| 4,434,156 | 2/1984 | Trowbridge | 424/85 |

FOREIGN PATENT DOCUMENTS

| | | | |
|---|---|---|---|
| 0075395 | 3/1983 | European Pat. Off. | 935/73 |
| 2094314 | 9/1982 | United Kingdom | 935/73 |

OTHER PUBLICATIONS

T. Maniatis et al, *Molecular Cloning, A Laboratory Manual*, pub. Cold Spring Harbor Laboratory, Cold Spring Harbor, N.Y., 1982, p. 313.

D. J. Kopecko et al., Abstracts of the Annual Meeting of the American Society for Microbiology, 1983, p. 60 (Abstract D9).

Engleberg, N. C. et al. "*Legionella pneumophila* Surface Antigens Cloned & Expressed in E. Coli are Translocated to the Host Cell Surface & Interact with Specific Anti-Legionella Antibodies" (1984), *J. Bacteriol.* 160:199.

Davis, G. S., Winn, W. C., Gump, D. W. & Beaty, H. N. "The Kinetics of Early Inflammatory Events During Experimental Pneumonia Due to *Legionella pneumophila* in Guinea Pigs" (1983), *Jrnl. Inf. Dis.*, 148:823–835.

Engleberg, N. C., Drutz, D. J., and Eisenstein, B. I. "Construction of a *Legionella pneumophila* Gene Bank", Legionella, Proc. 2nd Inter. Symp., (1984), presented to 2nd International Symposium on Jun. 20, 1983.

Pearlman, E., Drutz, D. J. and Eisenstein, B. I. "Identification of Surface Antigens of *Legionella pneumophila*", (1984) Abstract submitted for the 1984 American Society of Microbiology Meeting, presented to ASM on Mar. 4–9, 1984.

Engleberg, N. C., Pearlman, E., Drutz, D. J. and Eisenstein, B. I. "Cloned *Legionella pneumophila* Surface Antigens are Surface-Expressed in *E. coli*", Abstract, 1984 American Society of Microbiology Meeting (1984), presented to ASM on Mar. 4–9, 1984.

Engleberg, N. C., Drutz, D. J. and Eisenstein, B. I. "Cloning and Expression of *Legionella pneumophila* Antigens in *Escherichia coli*", *Inf. and Imm.*, 44:222 (May, 1984).

Nakamura, K., Pirtle, R. M. and Inouye, M. "Homology of the Gene Coating for Outer Membrane Lipoprotein within Various Gram-Negative Bacteria", *Jrnl. of Bacteriology*, 137:595–604 (1979).

Towbin, H., Staehelin, T., and Gordon J. "Electrophoretic Transfer of Proteins from Polyacrylamide Gels to Nitrocellulose Sheets: Procedure and Some Applications", *Proc. Natl. Acad. Sci. U.S.A.*, 76:4350–4354 (1979).

Meyer, T. F., Mlawer, N. and So, M. "Pilus Expression in *Nisseria gonorrhoeae* Involves Chromosomal Rearrangement", *Cell*, 30:45–52 (1982).

Clarke, L. and Carbon, J. "A Colony Bank Containing Synthetic Col El Hybrid Plasmids Representative of the Entire *E. coli* Genome", *Cell*, 9:91–99 (1976).

Brenner, D. J., Steigerwalt, A. G., Weaver, R. E., McDade, J. E., Feeley, J. C., and Mandel, M. "Classification of the Legionnaires' Disease Bacterium: An Interim Report", *Current Microbiol.* 1:71–75 (1978).

Engleberg, N. C., Drutz, D. J., Eisenstein B. I., "Cloning and Expression of *Legionella pneumophila* Antigens in *Eschericha coli*", Abstract, 23rd Interscience Conference on Antimicrobial Agents and Chemotherapy, (Oct. 24–26, 1983).

Primary Examiner—Sidney Marantz
Assistant Examiner—David A. Saunders
Attorney, Agent, or Firm—Arnold, White & Durkee

[57] ABSTRACT

Recombinant *E. coli* clones which cell surface-express *Legionella pneumophila* antigens, a method for utilizing these clones for the detection of Legionella antibodies in a clinical sample, and a method for isolation of monospecific anti-Legionella antibodies are disclosed. The recombinant clones are produced by ligating fragmented Legionella DNA to pBR322 which is then used to transform the appropriate *E. coli* host. Clones that cell surface-express individual Legionella antigens are selected by screening cellularly intact clones using anti-Legionella antibodies to probe for cell surface expression. An enzyme-linked immunosorbant assay (ELISA) is disclosed which utilizes the Legionella antigen-expressing clones to detect anti-Legionella antibodies.

18 Claims, No Drawings

METHODS AND COMPOSITIONS FOR DETECTION OF LEGIONNAIRES' DISEASE

BACKGROUND OF THE INVENTION

The present invention relates to methods and compostions for the detection of Legionnaires' desease and its causative agent, *Legionella pneumophila*, in an infected host. More specifically the methods described herein rely on the generation of immunologic antigen products specific for the detection of *Legionella pneumophila*-directed antibodies. These *Legionella pneumophila* antigen products are derived from a recombinant DNA clone bank comprised of *L. pneumophila* genes and expressed in an *E. coli* cloning host.

Current methods for the diagnosis of Legionnaires' disease in infected hosts are somewhat unreliable and generally result in a high level of falsely positive or falsely negative detections. Part of the problem in identifying the disease in a suspected carrier has been an inability to isolate the causative agent from the host. Successful isolation of the causative agent is required for conventional diagnosis of most bacterial infections. Alternative approaches to Legionnaires' disease detection include: (1) the staining characteristics and microscopic morphology of the *L. pneumophila* microorganism; (2) direct fluorescent staining of the microorganism with specific antiserum; and (3) the use of crude *L. pneumophila* antigens for the detection of circulating antibodies in an infected host.

Detection of Legionnaires' disease through the use of non-specific staining procedures has not proven to be a particularly sound basis for diagnosis. Although, *L. pneumophila* is a gram-negative organism, it stains poorly by conventional gram-staining techniques. Differential staining, where samples stained by the conventional gram method are compared to Lugol staining has been used to identify *L. pneumophila* organisms with varied success. Other non-specific stains have been tried, including Dieterle silver, Giemsa, methylene blue, and Gimenez, also with varied success (for a general discussion see Lattimer, G., *Legionnaires' Disease,* Marcel Decker, Inc., New York, 1981, pp. 65–81). These stains may be suggestive of the presence of *L. pneumophila* but are by no means definitive. They are useful only when no other bacteria are present or when examining infected tissue directly.

One approach to the identification of the organism is provided by direct fluorescent antibody staining with antisera directed to *L. pneumophila* antigens. Generally speaking, this method involves the generation of Legionella-directed antibodies in hyperimmune rabbit antisera followed by FITC conjugation of the antibodies. The FITC-conjugated anti-Legionella rabbit antisera is then reacted with slide-fixed suspected *L. pneumophila*-containing tissue, aspirate, or sputum samples. Some promising results have been demonstrated by this technique but caution must be exerted. First, most antisera are raised in rabbits with the aid of Freund's adjuvant, which contains mycobacterium. Therefore, the resulting rabbit Ig will often react with mycobacterium present in patient's sputum or pleural fluids. Second, antibodies may cross-react with a significant number of clinical isolates of *Bacteroides fragilis.*

Therefore, while the direct immuno-fluoresence test remains the method of choice for quick identification of the *L. pneumophila* organism it still suffers from many of the above-mentioned drawbacks. The technique requires an active sputum, pleural, or tissue sample containing the bacterium, which may not be available at the earlier stages of the disease, when rapid detection is of primary importance. In addition, the sensitivity of the direct immunofluorescence test is low, and therefore only about 60–75% of active cases are detected.

Another approach to the diagnosis of Legionnaires' disease, which is now the accepted standard, involves detecting circulating antibodies formed in the infected host in response to antigens present on the surface of the *L. pneumophila* bacterium. This has been accomplished by first inactivating the *L. pneumophila* organisms by either formaldehyde or steam killing and using the fixed bacteria in an indirect immunofluorescent assay for the detection of reacting antibodies in the suspected host. The assay requires both acute and convalescent serum samples and is not interpretable when performed on single serum samples during infection because of high background levels of non-specific antibodies. It has been suggested that the primary reason for the high level of nonspecific reactions in this diagnostic procedure is the presence of *L. pneumophila* cellular antigens that cross-react with other common bacteria to which humans are exposed. To produce a specific immunoassay, it would therefore be essential to separate specific from cross-reactive *L. pneumophila* antigens.

Therefore, in light of the above drawbacks in present Legionnaires' disease diagnosis, a technique which is both rapid, sensitive, and specific is needed in order to detect the presence of the disease early on, and diagnose it correctly and reproducibly. One such approach would be to utilize recombinant DNA technology whereby genes specific to *L. pneumophila* are used to specifically detect, by nucleic acid hybridization, the presence of *L. pneumophila* organisms in clinical samples. Owing to the specificity inherent in nucleic acid hybridization, such a technique should be capable of detecting the bacterium at extremely low levels in, for instance, sputum or pleural samples. A second possible detection method, which is provided by the present invention, is availed by the successful isolation of individual antigen molecules from *L. pneumophila.* Such antigens could then be used either directly to detect circulating antibodies, or to prepare highly specific antibodies or hybridomas. Antigens or antibodies prepared in this manner could be selected so as to be highly specific.

SUMMARY OF THE INVENTION

In its broadest scope, the present invention provides methods for producing and selecting recombinant cells which surface-express individual *Legionella pneumophila* surface antigens. The resultant selected recombinant clones, in addition to cell-surface expressing homophenotypic proteins, transcribe and translate the heterologous Legionella antigen gene, and insert at least a portion of the translated antigenic product into their cell envelopes.

In accordance with the present invention, *Legionella pneumophila* DNA, fragmented and then ligated to an appropriate vector, is used to transform an appropriate cloning host cell. The resultant recombinant cells are screened in such a manner so as to detect those recombinant clones which not only express an individual Legionella antigen, but also transport the heterologous antigen to the cell surfaces. In a preferred embodiment, the Legionella DNA is fragmented with a restriction endonuclease, ligated to DNA within the tetracycline-resistance gene of plasmid pBR322, and the resultant recombinant plasmid used to transform *E. coli* cells. It is contemplated by the inventor that other cloning systems, including yeast, higher eukaryotes, and other bacterial systems, can be used in place of the pBR322/*E. coli* system described herein.

Individual *Legionella pneumophila* antigens are identified using pre-adsorbed rabbit antisera directed against whole Legionella cells. In accordance with the present invention, recombinant clones bearing Legionella DNA are screened with the Legionella-directed antisera in such a manner so as to detect those recombinant clones which express Legionella antigens on their cell surface. In a preferred embodiment, this is accomplished by first depositing individual clonal colonies of the transformed cells on a solid support in such a manner so as to prevent lysis of the individual recombinant cells. The recombinant clone cells are then screened for the presence of Legionella antigens on their cell surfaces using labeled anti-Legionella antibodies which had been preadsorbed with whole *E. coli* cells.

In particular, the present invention identifies three individual Legionella antigens, namely, antigens migrating to a position corresponding to 19K (where k is defined as kilodaltons), 24K, and 66/68K by gel electrophoresis. Practice of the present invention has generated three individual recombinant clones, ATCC#'s 39724, 39725, and 39726, whose cell surfaces express the 19K, 66/68K, and 24K Legionella antigens, respectively.

The present invention is predicated upon the use of the selected recombinant clones in a whole cell ELISA assay to detect the presence of anti-*Legionella pneumophila* antibodies in a clinical sample suspected of containing such antibodies. Accordingly, the present invention is of significant utility in diagnosing Legionnaire's disease based on an ability to detect specifically and early in the course of the disease the presence of circulating anti-Legionella antibodies in clinical samples.

DETAILED DESCRIPTION OF THE INVENTION

Immunologic diagnosis of a pathogenic disease state normally requires either an antibody that is specific for antigenic determinents located on the pathogen itself or an antigen that is specifically expressed by the pathogen and not expressed in other pathogenic organisms. Whereas a monospecific antibody would be useful in the identification and speciation of suspected pathogens, they are of little diagnostic utility in the absence of clinical samples which contain the suspected pathogen. When such an "active" clinical sample is unavailable, as is generally the case in Legionnaires' disease, an antigen which is specifically expressed by the pathogen can be utilized to detect circulating antibodies directed against the pathogen by an infected immunocompetent host.

Detection of circulating antibodies is often accomplished through the use of an ELISA utilizing the pathogen-specific antigen. Although whole pathogen cells may be incorporated directly into a whole cell ELISA to detect antibodies directed against the pathogen (or in more standard form, in the indirect fluorescent assay), these approaches are often of little diagnostic utility during the acute illness. Due to the presence of cross-reacting antigens on the surface of *L. pneumophila* cells, patients sera must be tested at various time intervals for a four-fold increase in reactive antibody titer. Therefore, the present indirect fluorescent antibody assay is of little utility in diagnosing Legionnaires' disease where there is a premium on rapid, positive identification of the disease state.

Due to the cross-reactvity observed between antigens located on the cell-surface of *L. pneumophila* cells and similar antigens present on the cell surface of other microorganisms, the use of *L. pneumophila* cells directly in a whole cell ELISA is not determinative of anti-Legionella antibodies or Legionnaires' disease. Therefore, the present invention is predicated on the identification of antigens that are not cross-reacting and are thus specific to *L. pneumophila.* Practice of the present invention utilizes recombinant DNA technology to obtain expression of individual Legionella antigens in a heterogeneic organism such as *E. coli.* Moreover, techniques described herein provide for the selection of recombinant clone cells which have incorporated an individual Legionella antigen into their cell surface. These recombinant cells can therefore detect specific anti-Legionella antibodies using a whole cell ELISA in conjunction with whole *E. coli* cells as a control and thus avoid the necessity of collecting paired sera at various time intervals.

Although the present invention has been constructed utilizing an *E. coli* host/vector system, by way of example it is contemplated by the inventors that other cloning systems would function equally well. For example, numerous hosts other than *E. coli* have been successfully employed for recombinant DNA cloning including not only bacterial but eukaryotic and plant cell hosts as well. Moreover, a number of suitable vectors are currently available for use in the various hosts. For example, bacteriophage vectors such as lambda phage are commonly used in place of bacterial plasmids when a bacterial host is utilized. Alternatively, when a eukaryotic host, such as cultured mammalian cells are utilized, one may employ a viral vector such as SV-40.

The initial step in the practice of the present invention is the construction of a recombinant clone bank utilizing *Legionella pneumophila* DNA and the preparation of antisera directed against Legionella cells. The antisera is pre-adsorbed against the cloning host in order to remove cross-reacting antibodies. This preabsorbed antisera is then utilized to probe for expression of Legionella antigens on individual clones of the recombinant cells, thus allowing for the selection of recombinant clones which are useful in the diagnosis of Legionnaires' disease. Following initial identifications of clones which do cell surface express Legionella antigens, the clones are further characterized in order to identify and characterize the Legionella antigen that is being expressed in the recombinant clone.

MATERIALS AND METHODS

Bacterial Staining

*L. pneumophila* serogroup 1(130b), a clinical isolate from Wadworth Veterans Administration Hospital in Los Angeles provided by Paul Edelstein, M.D, was used for all cloning procedures and antigen preparations. For both purposes, *L. pneumophila* was isolated from infected guinea pigs and passed only once in buffered charcoal-yeast extract agar. *E. coli* K-12 strain HB101 ($m_{k^-}$, $r_{k^-}$, recA), and HB101 (pBR322) were obtained from Jack Jacobs, M.D., Department of Medicine, University of Texas Health Science Center, San Antonio, Tex.

Enzymes and Chemicals

Restriction endonucleases and T4 DNA ligase were obtained from Bethesda Research Laboratories, Bethesda, Md. Calf intestinal alkaline phospatase, lysozyme (grade 1), protein A-Sepharose, 5-amino-salicylic acid, ampicillin, and tetracycline were purchased from Sigma Chemical Co., St. Louis, Mo. Horseradish peroxidase-conjugated goat anti-rabbit immunoglobulin was purchased from Cappell Laboratories, Cochranville, Pa. The color-forming reagent 4-chloro-1-naphthol and nitrocellulose paper for electroblotting were purchased from Bio-Rad Laboratories, Richmond, Calif. Nitrocellulose disks for filter binding assays (type HA) were purchased from Millipore Corp., Bedford, Mass.; Whatman 3MM chromatography paper was obtained from American Scientific Products, McGaw Park, Ill. Fluorescein-labeled, polyvalent rabbit anti-Legionella antisera was obtained from the Center for Disease Control, Atlanta, Ga.

Preparation of L. Pneumophila Cells for Immunization

L. pneumophila cells from six buffered charcoal-yeast extract agar plates were harvested, pooled, and suspended in 6 ml of PBS(pH 7.3). Formalin-killed cells were prepared from 3 ml of this suspension by adding Formalin to a final concentration of 2.0% and holding overnight at 4° C. Heat-killed cells were prepared by heating the remaining 3 ml of suspended cells to 100° C. for 30 minutes. Both preparations were checked for nonviability at 24 hours.

Preparation of Antisera

New Zealand rabbits were injected subcutaneously with 2 ml of heat-killed (1:5 dilution) or formalin-killed *L. pneumophila* (1:10 dilution) cells at 0, 2, 4 and 6 weeks. Four rabbits were immunized: two received heat-killed cells and two received formalin-killed cells. Sera were collected at 7 weeks or later and were stored along with preimmune sera at −70° C.

Immune sera (0.5 ml samples) were absorbed 4 times with *E. coli* HB101 (pBR322) to remove antibodies that cross-react with *E. coli* (pBR322) antigens. For each absorption, cells from 175 ml of a stationary-phase culture were washed, mixed with sera, and rotated at 4° C. for 1 hour. Sera were recovered by centrifugation at 5,000×g for 5 minutes after each absorption. Sera used for the filter-binding assay were also absorbed with cells harvested from Luria-Bertani (LB) agar plates and with sonicated *E. coli* cells. For the sonicate absorption, cells from 500 ml of stationary-phase growth suspended in 10 ml of PBS were disrupted with a Branson Sonifer probe sonicator and then mixed with sera for 1 hour at 4° C. The serum-sonicate mixture was cleared by centrifugation at 100,000×g for 1 hour in a Beckman SW 40 rotor. Fifty microliters of *E. coli*-absorbed serum was also absorbed twice with mixtures of 0.1 ml of formalin-killed and 0.1 ml of heat-killed *L. pneumophila* cells for 8 hours at 4° C. All sera were heated to 56° C. for 30 minutes before use: the coagulum that formed in the serum-sonicate mixture was pelleted and removed by centrifugation at 10,000×g for 5 minutes. At this point, the sera are relatively free of anti-*E. coli* antibodies but retain antibodies against *L. pneumophila* antigens.

ELISA Test of Polyvalent Rabbit Antisera for Anti-Legionella Activity

Sera were tested for anti-*L. pneumophila* activity by an enzyme-linked immunosorbent assay (ELISA) using whole *L. pneumophila* cells fixed to 96-well microtiter plates. Formalin-killed *L. pneumophila* cells, corrected to an optical density at 550 nm of 1.5 with phosphate-buffered saline (pH 7.2) (PBS), and where then further diluted 1:25 with PBS. A 0.1-ml sample of dilute formalin-killed cells was added to each well, and the microtiter plates were allowed to dry overnight at 42° C. In this manner, the formalin-killed cells become fixed to the wells of the microtiter dish. Plates were washed three times with PBS containing 0.05% Tween 20 (polyoxyethylene 20), then serial dilutions of test sera (0.1-ml samples) were added, and plates were incubated for 2 hours at room temperature on a Minimix agitator (Fisher Scientific Co., Silver Sring, Md.). After three washes with PBS-0.05% Tween 20 (polyoxyethylene 20), 0.1 ml of peroxidase-conjugated goat anti-rabbit immunoglobulin (1:1,500 dilution) was added to each well, and the plates were again agitated for 2 hours. After three final washes with PBS-0.05% Tween 20 (polyoxyethylene 20), 0.1 ml of a color-forming substrate solution (0.08% 5-aminosalicylic acid and 0.006% hydrogen peroxide, pH 6.0) was added to each well. After agitation for 30 minutes, absorbance at 450 nm was measured in a MR580 MicroElisa Auto Reader (Dynatech) a spectrophotometric instrument designed to determine the absorbance of small aqueous samples and adapted for use in conjunction with the ELISA assay. An absorbance of 0.5 or more was considered positive.

To assess the effectiveness of serum absorption, a similar ELISA test was used in which live *E. coli* whole cells were fixed to the microtiter plate wells by the methods described above.

Rabbits immunized with either formalin-killed or heat-killed cells developed antibody titers of 1:1280 or greater as measured by the formalin-killed (whole cell) ELISA. Anti-*L. pneumophila* activity was not detected in any preimmune serum at titers of 1:10 or greater. Absorption of antisera with *E. coli* did not reduce the anti-*L. pneumophila* activity by more than one dilution, but did reduce the anti-*E. coli* titer from 1:320 to 1:40 in the *E. coli* whole cell ELISA.

EXAMPLE I: THE CLONE BANK

Preparation

DNA was extracted from *L. pneumophila* cells harvested from buffered charcoal-yeast extract agar plates in phosphate-buffered saline (PBS), pH 7.2. To assure against contaminating bacteria, samples of this supension were plated on buffered charcoal-yeast extract and sheep blood agar and inoculated into brain heart infusion broth. There was no growth on blood agar or brain heart infusion broth. Pure growth of *L. pneumophila* was detected on buffered charcoal-yeast extract agar and was confirmed by direct immunofluorescence with fluorescein-labeled, polyvalent rabbit antisera. *L. pneumophila* DNA was extracted and purified by a modification of the method of Nakamura et al. (Nakamura, K., Pirtle, R. M., and Inouye, M. (1979) *J. Bacteriol.* 137: 595–604) as follows:

*Legionella pneumophila* cells were harvested from four 72 hour BCYE agar plates and suspended in 5 ml of 50 mM Tris-HCl, pH 8.0 then centrifuged at 3000 rpm for 50 minutes to pellet the cells. The resultant cell pellet was resuspended in 1 ml of 25% sucrose-15 mM Tris-HCl, pH 8.0 and incubated at 37° for 30 minutes. 0.4 uL of 250 mM EDTA and 0.16 ml of 10% sodium dodecyl sulfate (SDS) were added and the suspension vortexed virgorously. 4 ml of a 20 mg/ml solution of proteinase K (Sigma Biochemicals) was added and the mixture incubated at 37° for 2 hours. This solution was then diluted by the addition of 2 ml of 50 mM Tris-HCl, pH 8.0.

The resultant DNA containing solution was extracted twice with an equal volume of phenol followed by two extractions with an equal volume of chloroform-:isoamyl alcohol (24:1). In both instances, the DNA remains in the aqueous layers and the organic layer was discarded. The DNA was then precipitated from the final aqueous layer by the addition of 100% ethanol and placement at $-20°$.

After 30 minutes at $-20°$, the DNA was pelleted at $30,000 \times g$ for 40 minutes. The resultant pellet was dried and resuspended in 2 ml of standard saline citrate (0.15M sodium chloride-0.015M sodium citrate) and 5 uL of a 20 mg/ml solution of DNase-free pancreatic RNase (Sigma) was added. This mixture was allowed to incubate at room temperature for 1 hour followed by the addition of 4 uL of a 20 mg/ml proteinase K solution. This mixture was allowed to incubate for an additional hour at 37°. The resultant DNA solution was again extracted with phenol and chloroform:isoamyl alcohol, ethanol precipitated, and pelleted as drescribed above. The final DNA pellet was resuspended in 0.5 ml 10 mM Tris-HCl, pH 8.0-1 mM EDTA and stored at 4° until used.

Purified DNA was partially restricted with Sau 3A restriction endonuclease, and the digestion fragments were applied to a 10 ml 5 to 40% sucrose gradient in 1M NaCl-20 mM Tris hydrochloride-5 mM EDTA (pH 8.0) and centrifuged at $100,000 \times g$ for 21 hours. Gradient fractions (0.5 ml) were analyzed by agarose gel electrophoresis, and fractions containing restriction fragments of 2.5 to 7.5 kilobase pairs were pooled.

Vector pBR322 was prepared for cloning by complete digestion with BamHI followed by 5' dephosphorylation with alkaline phosphatase. The latter procedure resulted in a 2- to 3-log reduction in recircularization and ligation of the vector as compared with untreated linear pBR322.

Size-fractionated $L.$ $pneumophila$ Sau 3A restriction fragments were ligated to dephosphorylated pBR322 with T4 DNA ligase and used to transform $E.$ $coli$ strain HB101 rendered conpetent by treatment with $CaCl_2$ as follows:

A fresh 3 ml overnight culture of *E. coli* HB101 was prepared in LB broth in a glass culture tube. 50 ml of this overnight culture was used to inoculate a fresh 3 ml aliquot of LB broth and the cells grown to an $O.D._{550}$ of 0.5, at which time the cells were chilled on ice. From this point on, unless otherwise indicated, all steps were performed on ice or in the cold. Following a 10 minute incubation on ice, the cells were pelleted, resuspended in 1.5 ml of ice-cold sterile 50 mM $CaCl_2$-50 mM Tris-HCl, pH 8.0, transferred to sterile 1.5 ml Eppendorff tubes, and incubated on ice for 15 minutes. The cells were then pelleted in an Eppendorff centrifuge for 2 minutes and the supernatent aspirated off and discarded. The cell pellet was then resuspended in 0.2 ml of the above calcium chloride solution and the cell suspension stored overnight at 4°.

The recombinant plasmid DNA to be used for transformation was diluted to 100 ul in 10 mM Tris-HCL, pH 8.0-1 mM EDTA and added to the above *E. coli* cells, vortexed gently, and placed on ice. After 30 minutes the cells were shock-treated by placement at 42° for 2 minutes, following which 1 ml LB broth containing 25 mg/ml ampicillin was added. After incubation at 37° for 1 hour, the cells were plated out on LB agar plates containing 40 ug/ml ampicillin. Transformants were selected on Luria-Bertani agar containing ampicillin (40 ug/ml). Forty ampicillin-resistant ($Ap^r$) transformants were screened for tetracycline sensitivity ($Tc^s$) on Luria-Bertani medium containing tetracycline (15 ug/ml).

*E. coli* HB101 was transformed using the above procedure at an efficiency of $10^3$ transformants per ug of vector DNA. A sample of 40 $Ap^r$ transformants was transferred to media containing tetracycline: all 40 were $Tc^s$.

Screening of Clone Bank for Antigen Expression $Ap^r$ transformants were then screened for detection of those recombinant clones exhibiting general Legionella antigen expression. The technique employed a cell lysis step and therefore was not specific for those recombinant clones exhibiting cell-surface expression of individual Legionella antigens. $Ap^r$ transformants were spotted onto agar plates with sterile toothpicks (ca. 325 colonies per plate), grown overnight, and then blotted onto dry nitrocellulose filter disks; 1 to 2 ul of formalin-killed *L. pneumophila* were also spotted onto each filter as a positive control. Colonies were lysed in situ by the method of Meyer et al. as follows (Meyer, T. F., Mlawer, N., and So, M. (1982). *Cell.* 30:45–52.):

Filter disks were placed sequentially, colony side up onto Whatmann 3 MM paper in a series of four petri dishes saturated respectively with (i) 0.1N NaOH, (ii) 1.5M Tris-hydrochloride (pH 7.4), (iii) 300 mM NaCl-30 mM sodium citrate, and (iv) 70% ethanol and 5 minutes each. Each filter was then dried in a vacuum at 60° C. for 2 hours. Antigen-bearing colonies were detected by an enzyme immunoassay as follows: Dry filters were placed in Tris-buffered saline (50 mM Tris-hydrochloride, 150 mM NaCl, pH 7.5) containing 3% gelatin to block nonspecific protein-binding sites. After gentle rotation at room temperature for 2 hours, the filters were transferred to a solution of *E. coli*-absorbed, pooled antisera prepared as described above (1:800 dilution in 1.5% gelatin-TBS) and incubated overnight at room temperature. The following morning, the filters were rinsed with distilled water, washed four times in TBS, and incubated in a solution of peroxidase-conjugated goat anti-rabbit immunoglobulin (1:3,000) for 2 hours. After a final rinse and series of four washes in TBS, the filters were immersed in a color development solution consisting of 0.05% 4-chloro-1-naphthol and 0.015% hydrogen peroxide in a 5:1 solution of TBS-methanol.

All colonies showing color development were reanalyzed by a modified filter bound immunoassay in which the alkaline lysis and neutralization steps (i.e., on saturated Whatmann 3 MM paper) were eliminated, and freshly blotted colonies were placed directly into the vacuum oven.

The above procedure was used to screen 2,559 $Ap^r$ transformants. 77 (3.0%) of these clones produced detectable blue color. Of these, 31 (1.20%) were considered to be strongly reactive, and 46 (1.8%) were considered weakly reactive. All 77 reactive clones were transferred to a single nitrocellulose disk and analyzed by the modified filter-bound immunoassay which excluded the chemical lysis steps. In this assay, 11 clones produced detectable color; 6 were strongly positive (clones 11, 13, 40, 41, 44, and 70), and 5 were weakly positive (cloness 33, 47, 61, 65, and 73). Of these 11 clones, 10 were also strongly reactive in the filter-bound immunoassay with cellular lysis; clone 47 was weakly reactive in both assays. Omission of the chemical lysis step in the filter-bound immunoassay procedure allows for the detection of some of the *E. coli* clones which actually have incorporated individual *L. pneumophila* antigens into the cell envelope of the *E. coli* clone cell. Additional clones exhibiting surface expression of *L. pneumophila* antigens were detected by other techniques employed in later examples.

EXAMPLE II: CHARACTERIZATION OF INDIVIDUAL *L. PNEUMOPHILA* ANTIGENS WHICH ARE SURFACE-EXPRESSED IN *E. COLI* CLONES

Protein immunoelectroblotting was employed to analyze the individual *L. pneumophila* antigens responsible for the strong reaction of those positive clones identified by the filter-bound immunoassay procedure. More specifically, 29 of the strongest reacting clones were analyzed by sodium dodecyl sulfate (SDS)-polyacrylamide gel electrophoresis and protein blotting, as described below, in order to determine the molecular weight of, and positively identify, Legionella-specific antigens.

Each clone was grown to the stationary phase in 3.0 ml of Luria-Berani (LB) broth containing ampicillin (50 ug/ml). Cultures were washed once with PBS, transferred to Eppendorf tubes, suspended in 0.375 ml of sample buffer (75 mM Tris-hydrochloride, 5% 2-mercaptoethanol, 2% SDS, 10% glycerol, 0.002% bromophenol blue, pH 6.8), and heated to 100° C. for 2.5 minutes. SDS-polyacrylamide gel electrophoresis was performed in a vertical slab gel electrophoresis tank (Hoefer Scientific Instruments, San Francisco, Calif.) by the method of Laemmli (Laemmli, U.K. (1970) *Nature* (London), 117:680-685) as follows:

Sample of 0.04 ml were run at 25 mA constant current through the 5% polyacrylamide stacking gel (pH 6.8) and at 50 mA through the 15% polyacrylamide separating gel (pH 8.3). Electrotransfer of proteins to nitrocellulose was performed in a Trans-Blot Cell (Bio-Rad) at 30 mV for 12 hours with a buffer containing 0.025M Tris base, 0.192M glycine, and 20% methanol (pH 8.3). Renatured proteins on nitrocellulose were visualized with an enzyme-linked immunoassay. First, nitrocellulose sheets were preincubated in a blocking solution of TBS with 0.05% Tween 20 (polyoxyethglene 20 ) and then transferred overnight to a similar solution containing 1:750 of the rabbit anti-Legionella antisera. After four washes with 0.05% Tween 20-TBS, sheets were incubated in a 1:3,000 dilution of peroxidase-conjugated goat anti-rabbit immunoglobulin in 0.05% Tween 20-TBS for one hour. After a rinse in distilled water and four additional 0.05% Tween 20-TBS washes, the sheets were exposed to color development reagent (0.05% 4-chloro-1-napthol and 0.015% hydrogen peroxide in a 5:1 solution of TBS:methanol). The molecular weight of each individual bank was estimated by comparing its coefficient of migration to a logarithmic plot for the migrations of protein standards run on the same gel and visualized with Coomassie blue stain.

Of the 29 strongly reactive clones that were analyzed by the protein immunoblotting techniques (two clones were unstable and could not be maintained in antibioticcontaining media), 18 had protein bands detected by protein blotting with *E. coli*-absorbed rabbit antiserum, but not with preimmune serum (see Table I below). Clones 11, 13, 40, 41, 44, and 70, which gave strong signals by filter-bound enzyme immunoassay with and without chemical lysis, all expressed the same antigenic proteins. These antigens appear as a confluence of bands in the 19 K to 24 K range. Because a faintly reactive 19 K to 20 K band was seen in immunoblots of all *E. coli* strains, we analyzed a representative clone (no. 11) by additional techniques to confirm the separate identity of the cloned antigens from the background band. Protein immunoblots, which were probed with unabsorbed antisera, confirmed that 19 K antigens are present in both the recipient *E. coli* strain and *L. pneumophila; E. coli* clone no. 11 expresses both reactivities. In addition, analysis of clone no. 11 by radioimmunoprecipitation with absorbed antisera resolved four bands of 19 K, 20 K, 23.5 K, and 28 K that are distinct from *E. coli* background antigens. Also in this analysis, an *E. coli* antigen between 19 K and 20 K was precipitated. None of the other cloned antigen bands that were identified by immunoblotting coincided with background antigenic bands. The following table, Table I, is a compilation of data obtained by the foregoing immunoblot screening of selected *E. coli* clones that cell surface-express individual *L. pneumophila* antigens.

TABLE I

Characterization of cloned *L. pneumophila* antigens

| *E. coli* transformants (isolate no.) | Molecular masses of cloned antigens |
|---|---|
| 50 | 68K |
| 63 | 61K |
| | 66K |
| 12 | 61K |
| | 66K |
| | 68K |
| 11, 13, 40, 41, 44, 70 | 19K to 23K[a] |
| 21, 31, 32, 43, 60, 71 | 24K |
| 47, 81, 82 | 17K |

[a]radio-immunoprecipitation resolved individual bands of 19K, 20K, 23K and 28K.

EXAMPLE III: IDENTIFICATION OF INDIVIDUAL *L. PNEUMOPHILA* ANTIGENS

The results of the protein immunoblotting technique demonstrated that of the 18 reactive clones identified, three classes of individual *L. pneumophila* antigens were characterized: one which migrated at a position corresponding to 19 K by gel electrophoresis (clone 11), one at 24 K (clone 21), and one at 66/68 K (clone 12). To comply with ATCC deposit requirements, these clones have been given the designations *E. coli* (pSMJ 11) (ATCC #39724), (pSMJ 21) (ATCC #39726), and (pSMJ 12) (ATCC #39725), respectively. These three clones, being the most highly reactive to *L. pneumophila*-directed antibodies, were reanalyzed numerous times by the protein immunoblotting technique described above.

To determine whether these recombinant cells expressed *L. pneumophila* antigens on their cell surface, the ability of these three representative strains to selectively absorb specific immunologic activity against the homologous cloned antigen from whole antisera was tested. In each case, absorption reduced antibody activity, assessed by immunoblotting, against the specific cloned antigen contained in the specific strain used for absorption. These findings are summarized below in Table II.

TABLE II
The Ability of Antigen - expressing Clones to Remove Specific Antibodies from Crude Anti-Legionella Antisera

| Strain Used For Absorption of Antisera | Antibody Reactivity After absorption | | |
|---|---|---|---|
| | 19K | 24K | 66/68K |
| E. coli (pBR322) | + | + | + |
| E. coli (pSMJ 11) | −* | + | + |
| E. coli (pSMJ 12) | + | + | − |
| E. coli (pSMJ 21) | + | − | + |

*Reduced, but not totally removed

In addition, we further proved the surface accessibility of the antigens to the antibodies by recovering the specific antibodies from washed cells by acid elution. The fact that these clones express L. pneumophila antigens on their surfaces was confirmed utilizing a liquid phase enzyme immunoassay. Briefly, this technique entails (1) selective absorption of pooled rabbit antisera to intact E. coli clones, (2) elution of the antibodies from the intact clone cells, and (3) reacting the eluted antibody in liquid phase with *L. pneumophila* cells. The liquid-phase immunoassay is described in detail under Example IV.

EXAMPLE IV: LIQUID-PHASE ENZYME IMMUNOASSAY FOR DETECTION OF SURFACE ANTIGENS

Absorption of Antisera to Intact Cells

Separate aliquots of pooled rabbit anti-*L. pneumophila* antisera were absorbed individually with *E. coli* (pBR322) and each of the *L. pneumophila* antigen-producing recombinant strains (Table I). 0.25 ml aliquots of pooled rabbit antisera, diluted 1:10 in PBS, were absorbed four times with washed intact cells (125 ml of stationery phase culture for each absorption) for 1 hour at 4° C. Sera were recovered between successive absorptions by cold centrifugation at 5000×g. After the fourth absorption, serum supernatants were collected and passed through a 0.22 micron Millipore filter.

Elution of Antibodies from Intact Cells 0.1 ml aliquots of rabbit antisera were mixed with washed cells (5 ml of stationery phase cultures of *E. coli* or an equivalent volume of *L. pneumophila* harvested from agar plates) and were rotated overnight at 4° C. Serum supernatants were discarded, and cell pellets were washed three times in PBS. After the final wash, the pellet was resuspended in 1.0 ml elution buffer (0.2M sodium chloride, 0.1M glycine, pH 2.8) and rotated for 30 minutes at room temperature. The cells were then repelleted, and the supernatant was removed, passed through a 0.22 um Millipore filter, and slowly titrated to pH 7.5 with 2M Tris. Using these methods, aliquots of antisera were absorbed to and eluted from the surface of *L. pneumophila, E. coli* HB 101 (pBR322), and each of the three antigen-expressing recombinant clones (see Table II).

Detection of Surface Antigens

Antibodies eluted from *L. pneumophila* and *E. coli* cells were each assayed for antibodies that react with surface components on cells of the opposite species. Stationary phase cells of *E. coli* (pBR322) and *E. coli* (pSMJ 11) were washed and ajusted to O.D.$_{550}$ 0.9 with PBS. 0.4 ml of the cell suspension was pelleted, resuspended in *L. pneumophila* eluate, and rotated at 4° C. for 4 hours. After three washes in PBS, the cells were resuspended in peroxidase-conjugated goat anti-rabbit IgG (1:1500 dilution) and incubated in the cold for an additional 2 hours. After three final washes in PBS, the final cell slurry was divided into eight equal aliquots and added to microtiter plate wells which contained a color-producing substrate (0.08% 5-aminosalicylic acid, 0.006% hydrogen peroxide, pH 6.0). Absorbance at 450 nm was read in a MR 580 MicroElisa Auto Reader (Dynatech) after 30 minutes agitation. The converse experiment (that is, the reaction of eluates from *E. coli* (pBR322) and *E. coli* (pSMJ11) with intact *L. pneumophila* cells) was also performed using the same methods.

The results of the liquid phase assay are shown below in Table III.

TABLE III

Detection of Surface-Reactive Antigen by Liquid-Phase ELISA Using Antibodies Eluted from Intact Cells of the Heterologous Species

| Target cells | First antibody | Second anti-body | Absorbance + S.D. |
|---|---|---|---|
| *E. coli* (pBR322) | − | − | .004 + .009 |
| *E. coli* (pBR322) | − | + | .009 + .009 |
| *E. coli* (pBR322) | *L. pneumophila* true (serum) eluate | + | 015 + .009 |
| *E. coli* (pSMJ 11) | *L. pneumophila* true (serum) eluate | + | .047 + .010 |
| *E. coli* (pSMJ 21) | *L. pneumophila* true (serum) eluate | + | .077 + .005 |
| *L. pneumophila* | *E. coli* (pBR322) sham (PBS) eluate | + | .006 + .030 |
| *L. pneumophila* | *E. coli* (pBR322) true (serum) eluate | + | .012 + .017 |
| *L. pneumophila* | *E. coli* (pSMJ 11) | + | .077 + .013 |
| *L. pneumophila* | *E. coli* (pSMJ 21) true (serum) eluate | + | .151 + .032 |

EXAMPLE V: DETECTION OF SERUM ANTIBODY BY RECOMBINANT CLONE ELISA

Intact cell ELISA was performed as described above, except that cells were resuspended to O.D.$_{550}$ 0.9 and diluted 1:8 in 5 mM phosphate buffer before distribution into microtiter wells. Serial dilutions of antisera were tested in adjacent rows of wells containing either *E. coli* (pBR322) or *E. coli* (pSMJ11) cells. When serial dilutions of rabbit immune sera were tested by the intact cell ELISA, reactivity against cells containing a hybrid plasmid, *E. coli* (pSMJ11), was relatively greater than against the control strain, *E. coli* (pBR322), at dilutions greater than 1:500. In contrast, reactivity against these two whole cell antigens was similar in dilutions of either pre-immune rabbit antisera or rabbit anti-*E. coli* immune serum. When the differential reactivity of each sera is plotted as a function of serum dilution, anti-*L. pneumophila* sera were clearly distinguished from the two other control sera. The results, therefore, demonstrate that *E. coli* (pSMJ11), can successfully be used to detect the presence of Legionella-directed antibodies in a non-specific mixture of the antibodies.

Furthermore, similar studies utilizing *E. coli* (pSMJ12) and (pSMJ21) which cell surface express the individual 66 K/68 K and 24 K *Legionella pneumophila* antigens, respectively, demonstrate that these clones can also be used to detect the presence of Legionella-directed antibodies in a non-specific mixture of antibodies. For example, pooled rabbit antisera (diluted 1:500)

was tested for immunoactivity versus *E. coli* (pSMJ21) in a whole-cell ELISA. Controls utilizing *E. coli* (pBR322) exhibited an average absorbance at 450 nm of 0.4 or less. When the same antisera was tested versus *E. coli* (pSMJ21), absorbances ranging from 1.0, at an antigen dilution of 1:32, down to approximately 0.7 antigen diluting of 1:1 or 1:128 were obtained. When sera which had been preabsorbed with *E. coli* (pSMJ21) cells was tested, the ELISA immunoreactivity returned to control levels.

EXAMPLE VI: LEGIONNAIRES' DISEASE CLINCIAL MODEL

An animal model of Legionnaires' Disease has been developed in guinea pigs by Dr. Jim Williams of the National Institute of Health. In this model, Male Hartley strain guinea pigs are infected with clinical isolates of serogroup 1 *L. pneumophila.* Control sera, and sera obtained from 10 and 33-day post infection guinea pigs, were provided by Dr. Williams to demonstrate the utility of the present invention. Included in this study were sera from guinea pigs infected with the Philadelphia-S strain of *L. pneumophila* serogroup 1.

The sera were subjected to the whole cell ELISA assay described above utilizing *E. coli* (pSMJ11). Sera taken from control guinea pigs demonstrated no appreciable immunoreactivity. Conversely, sera from animals, 10-day post-infection with Philadelphia-S strain, demonstrated appreciable immunoreactivity at serum dilutions down to 1:320. Likewise, sera obtained from 33-day post-Philadelphia-S infection guinea pigs demonstrated appreciable immunoreactivity at sera dilutions down to 1:80.

The foregoing invention has been described in some detail by way of illustration and example and in terms of standard laboratory techniques employed by the applicant. It will be apparent to those skilled in the art that certain changes and modifications of these procedures may be employed without departing from the spirit and scope of the invention. For example, although the Legionella DNA used for cloning was fragmented by partial digestion of the DNA with restriction endonuclease Sau 3A, partial digestion with other restriction endonucleases or by mechanical shearing, would function equally well. Or, although a standard ELISA method is described, there is no reason to suspect that this general scheme would not be equally (or even beter) suited to use with other detection methods in routine solid-phase antibody-detection assays. Such an assay would be most useful for rapid diagnosis if an IgM-specific conjugated antibody is substituted for the second antibody that is currently being used. Moreover, it will be apparent to those skilled in the art that such modifications and changes are within the scope of the appended claims.

What is claimed is:

1. A method for providing recombinant *E. coli* cells, which cells express individual *Legionella pneumophila* antigens, the method comprising the steps of:

(a) transforming *E. coli* cells with *Legionella pneumophila* DNA;

(b) screening clonal colonies of the transformed cells to identify those cells which express a 19 K, 24 K or 66/68 K *Legionella pneumophila* antigen; and (c) culturing cells identified in step (b) to provide the recombinant cells.

2. The method of claim 1 wherein screening the clonal colonies of the transformed cells to identify those cells which express the 19 K, 24 K or 66/68 K *Legionella pneumophila*-specific antigen comprises:

(a) depositing individual clonal colonies of the transformed cells on a solid support;

(b) obtaining an antibody-containing composition which includes antibodies having immunospecificity for the 19 K, 24 K or 66/68 K *Legionella pneumophila*-specific antigens, the composition being substantially free of antibodies which cross-react with *E. coli* antigens;

(c) placing the antibody - containing composition in contact with the solid support in such a manner as to allow for immuno-complex formation between antibodies of the composition and *Legionella pneumophila* antigens expressed by individual clonal colonies; and (d) identifying those clonal colonies which express the 19K, 24K or 66/68K *Legionella pneumophila*-specific antigens by means of a label.

3. The recombinant cells made by the process of claim 1.

4. The method of claim 1 wherein the *Legionella pneumophila* antigen is expressed on the cell surface of the recombinant *E. coli* cell and step (b) comprises screening clonal colonies of the transformed cells to identify those cells which cell-surface express the 19K, 24K or 66/68K *Legionella pneumophila* antigen.

5. The method of claim 4 wherein screening the clonal colonies of the transformed cells to identify those cells which cell surface express the 19K, 24K or 66/68K *Legionella pneumophila*-specific antigen comprises:

(a) depositing individual clonal colonies of the transformed cells on a solid support in such a manner so as to prevent lysis of the individual bacterial cells;

(b) obtaining an antibody-containing composition which includes antibodies having immunospecificity for the 19K, 24K or 66/68 *Legionella pneumophila*-specific antigens, the composition being substantially free of antibodies which cross-react with *E. coli* antigens;

(c) placing the antibody-containing composition in contact with the solid support in such a manner as to allow the immuno-complex formation between antibodies of the composition and *Legionella pneumophila* antigens expressed by individual clonal colonies; and (d) identifying those clonal colonies which cell surface-express the 19K, 24K or 66/68K *Legionella pneumophila*-specific antigens by means of a label.

6. The method of claim 1 wherein transforming the cells comprises:

(a) fragmenting the *Legionella pneumophila* DNA;

(b) ligating the fragmented DNA to a cloning vehicle; and (c) transforming the cells with the recombined cloning vehicle.

7. The method of claim 6 wherein fragmenting the DNA comprises:

(a) performing a partial restriction endonuclease digestion with restriction endonuclease Sau 3A;

(b) fractionating the partially restricted DNA according to molecular mass; and (c) pooling those DNA fragments exhibiting a molecular mass corresponding to a fragment length of 2.5 to 7.5 kilobase pairs.

8. The method of claim 6 wherein the suitable cloning vehicle is the plasmid pBR322 which has been predigested with the restriction endonuclease Bam HI.

9. A recombinant *E. coli* cell that expresses a 19K, 24K or 66/68K *Legionella pneumophila*-specific antigen.

10. The recombinant cell of claim 9 wherein the *Legionella pneumophila* antigen is expressed on the cell surface of the recombinant cell.

11. The recombinant cell of claim 9 wherein the antigen is coded for by a recombinant vector comprising *Legionella pneumophila* DNA fragments ligated to the cloning vector.

12. The recombinant cell of claim 11 wherein the *Legionella pneumophila* DNA fragments are obtained by restriction endonuclease digestion of the *Legionella pneumophila* DNA with the restriction endonuclease Sau 3A.

13. The recombinant cell of claim 11 wherein the cloning vector is pBR322.

14. The recombinant cell *E. coli* (pSMJ 11) (ATCC #39724), which cell surface expresses the individual 19K *Legionella pneumophila* antigen.

15. The recombinant cell *E. coli* (pSMJ 21) (ATCC #39726), which cell surface expresses the 24K individual *Legionella pneumophila* antigen.

16. The recombinant cell *E. coli* (pSMJ 12) (ATCC #39725), which cell surface expresses the individual 66/68K *Legionella pneumophila* antigen.

17. A method for detecting the presence of anti-*Legionella pneumophila* antibodies in a clinical sample suspected of containing the antibodies which comprises performing a whole cell ELISA on the clinical sample utilizing the recombinant cells of claims 9, 10, 11, 12, 14, 15, or 16.

18. A method for detecting the presence of anti-*Legionella pneumophila* antibodies in a clinical sample suspected of containing the antibodies comprising the steps of:
(a) contacting the sample with the recombinant cell of claim 3, 9, 10, 11, 12, 14, 15, or 16 under conditions which will promote specific antigen/antibody immunocomplex formation between antigens contained by the cell and antibodies present in the sample; and
(b) detecting such immunocomplex formation by means of a label to thereby detect the presence of anti-*Legionella pneumophila* antibodies in the sample.

* * * * *